(12) United States Patent
Bauer

(10) Patent No.: US 7,780,541 B2
(45) Date of Patent: Aug. 24, 2010

(54) GOLF TRAINING GLOVE

(76) Inventor: David Bauer, Neupforte 15, Aachen (DE) D-52062

( * ) Notice: Subject to any disclaimer, the term of this patent is extended or adjusted under 35 U.S.C. 154(b) by 360 days.

(21) Appl. No.: 11/912,001

(22) PCT Filed: Mar. 27, 2006

(86) PCT No.: PCT/EP2006/002772

§ 371 (c)(1),
(2), (4) Date: Oct. 19, 2007

(87) PCT Pub. No.: WO2006/111245

PCT Pub. Date: Oct. 26, 2006

(65) Prior Publication Data

US 2008/0189827 A1 Aug. 14, 2008

(30) Foreign Application Priority Data

Apr. 20, 2005 (DE) .................. 10 2005 018 527

(51) Int. Cl.
 *A63B 69/36* (2006.01)
 *A41D 19/00* (2006.01)
 *A63B 71/14* (2006.01)
(52) U.S. Cl. .................. 473/205; 473/202; 473/409; 434/252; 2/161.2
(58) Field of Classification Search .................. 473/201, 473/202, 205, 207, 212, 409; 434/252, 365, 434/392; 2/161.1, 161.2, 161.3, 161.4, 161.6, 2/160, 163
See application file for complete search history.

(56) References Cited

U.S. PATENT DOCUMENTS

| 4,488,726 | A | * | 12/1984 | Murray ................ 473/202 |
| 5,221,088 | A | | 6/1993 | McTeigue et al. |
| 5,655,223 | A | | 8/1997 | Cozza |
| 5,681,993 | A | | 10/1997 | Heitman |
| 5,733,201 | A | | 3/1998 | Caldwell et al. |
| 5,771,492 | A | * | 6/1998 | Cozza ................ 2/161.2 |
| 6,016,103 | A | | 1/2000 | Leavitt |
| 2002/0129437 | A1 | | 9/2002 | Erker |
| 2002/0194668 | A1 | | 12/2002 | Kwon |

FOREIGN PATENT DOCUMENTS

| DE | 4240531 C1 | 2/1994 |
| DE | 19854237 A1 | 2/2000 |
| GB | 2120082 A | 11/1983 |
| WO | 0001303 A1 | 1/2000 |

* cited by examiner

*Primary Examiner*—Nini Legesse
(74) *Attorney, Agent, or Firm*—Brooks Kushman P.C.

(57) ABSTRACT

The invention relates to a golf training glove with sensors for triggering a perceptible signal on an erroneous gripping technique of the golf club with glove fingers to accommodate the thumb, index finger, middle finger, ring finger and little finger. According to the invention, error signals with a correct gripping technique may be avoided, whereby the sensors are at least arranged on the glove fingers for accommodation of the index finger, middle finger and ring finger and the perceptible signal is triggered by an excessive gripping pressure. No sensor is arranged on the thumb of the golf training glove.

22 Claims, 7 Drawing Sheets

GOLF TRAINING GLOVE

The invention relates to a golf training glove having sensors for triggering a perceptible signal when the technique used to grip the golf club is incorrect and having glove fingers for accommodating the thumb, index finger, middle finger, ring finger and little finger.

Training aids for golf players, which are essentially aimed at mechanical aspects of the golf swing and are intended to make it easier for the player to learn correct positions and directions of movement in particular swing phases, currently exist. However, a further important aspect is ignored or even prevented in this case, namely that the player should swing without putting excessive stress on the body as far as possible. This tension has a plurality of harmful effects:

Tensioned wrists prevent the movement energy which is stored in the club head from being discharged or result in it being discharged at the wrong point in time.

Tensioned forearms block mutual rotation of the forearms and so-called release of the club head, which results in a reduced speed of the club head and incorrect orientation of the club face at the time of hitting the ball.

Particular muscle areas in the body work against one another and reduce the swing speed by blocking the natural movement of the club.

A golf player who is not aware of these relationships will, with the intention of wanting to hit the ball as far as possible, build up harmful stress in the hands (and consequently in the forearms and other parts of the body) and will achieve the exact opposite, namely strokes which are too short and imprecise.

GB 21 20 082 A discloses a golf training glove which automatically generates an acoustic alarm signal if the grip strength loosens during the golf stroke. In order to signal this loosening of the grip strength, the golf training glove has pressure-actuated switches on the inside of the glove. A respective switch is situated on each finger and on the thumb. In addition, a further switch is arranged on the outside of the palm. The pressure-actuated switches are preferably connected in parallel with one another as interrupters. The switches which are connected in parallel are in series with a battery and a buzzer. As long as the golf grip is held in a sufficiently firm manner, the ten interrupter switches are open and the buzzer does not generate an acoustic signal. However, if the grip is released, with the result that one of the switches closes, the acoustic signal is generated.

This solution only makes it possible to ensure that the golf club is held with a minimum force. However, the arrangement of sensors is not able to monitor and avoid undesirable harmful stresses in the hands.

U.S. Pat. No. 5,655,223 discloses a golf training glove which generates perceptible signals when the grip is loosened during the swing. For this purpose, the golf training glove has a pressure-dependent sensor in the region of the palm and the rear side of the thumb. The sensor arranged at the base of the thumb responds if, in the case of the conventional overlapping grip, the trailing hand is loosened. The sensor arranged in the palm is intended to respond in the case of an excessively wide swinging movement in which the lead hand is unintentionally loosened.

This golf training glove too cannot avoid harmful stresses being built up in the hands and excessively short and imprecise strokes being carried out as a result. Rather, the opposite is the case. If the golf club is held with a high level of muscle tension, that is to say clenched, the signal transmitters do not respond at all on account of this golf training glove.

U.S. Pat. No. 2002/0129437 A1 discloses a pressure sensor in the thumb of a golf training glove. The problem in this case is that a player is easily able to firmly grip the club with his fingers and nevertheless allow the thumb to relax or even protrude from the grip. In this case, the effect where the thumb can be controlled relatively independently of the remaining fingers becomes important. A further disadvantage is that, even in the case of a fully relaxed gripping pressure, the weight of the club must be downwardly supported by both thumbs at the upper reversal point of the swing. As a result of the fact that the center of gravity of the club is at a considerable distance from the grip, the force on the thumbs is intensified as a result of a lever effect, with the result that the stated triggering threshold of 600-700 g is exceeded to a considerable extent.

U.S. Pat. No. 2002/0194668 A1 discloses the practice of installing a pressure sensor in the glove for the left hand, said pressure sensor being under the bases of the fingers on the upper inner surface of the hand. This idea is based on the assumption that the club rests along this line in the case of a correct gripping technique and is pressed into the pressure sensor by the fingers. An inexperienced golf player with a poor gripping technique will not push the club into the region of the pressure sensor in a reliable manner. The fact of whether the club grip does not overlap or only partially overlaps the pressure sensor is also problematic. However, the following disadvantages are far more serious: with a correct swinging technique, the club should be pushed away with the left hand at the beginning of the swing and not pulled away with the right hand. As a result of incorrectly pulling away with the right hand, the fingers must automatically tense in order to counteract the inertia of the club, while the correct initiation of the swing with the left hand does not build up any harmful stress since all of the fingers can remain relaxed. However, with the correct technique for initiating the swing, a force is exerted on the pressure sensor on the inner surface of the hand as a result of the inertia of the club counter to the direction of movement during the upswing, with the result that the sensor is triggered even with a completely relaxed, correct grip.

Just like when the pressure sensor is placed in the thumb in accordance with U.S. pat. No. 2002/0129437A1, another disadvantage is that a great force is exerted on the pressure sensor in the palm at the upper reversal point since the inner surface of the left hand upwardly supports the weight of the club. This force is even greater than the force on the thumbs since the only upwardly effective force occurs at this point when the forces are in equilibrium. Furthermore, in this solution, the pressure sensor is installed only in the left glove since, for reasons of swing theory, an increased gripping pressure in the left hand has more harmful effects than in the right hand. However, it is also desirable to monitor the gripping pressure of the right hand because a golf player is able to consciously or unconsciously build up a different gripping pressure in both hands without problems.

On the basis of this prior art, the invention is based on the object of providing a golf training glove which does not have the abovementioned disadvantages, in particular does not produce any incorrect signaling with a correct gripping technique and in the process assists the player in avoiding harmful stress in the hands during the golf swing.

The invention is based on the concept of the fingers enclosing the grip and, as actuators, building up the actual gripping pressure. A measurement at this point provides the results which have been corrupted least.

Specifically, the object is achieved in the case of a golf training glove of the type mentioned initially by virtue of the fact that the sensors are arranged at least in the glove fingers for accommodating the index finger, middle finger and ring finger and trigger the perceptible signal in the case of an excessively high gripping pressure.

The perceptible signal is triggered, in particular, by evaluation electronics if a threshold value comparison of the measured values recorded by the sensors with at least one threshold value reveals that an excessively high gripping pressure has been built up. Placing a sensor in the thumb is preferably dispensed with since the pressure sensor in the thumb of the glove is responsible, in particular, for incorrect signaling.

The pressure sensors are preferably installed in all glove fingers, apart from the thumb, of the golf training glove both for the left hand and for the right hand.

In one preferred refinement of the invention, the sensors are incorporated in a pocket which is formed by a double outer skin on the inside of the finger.

Electrical and pneumoelectrical sensors are suitable, in particular, as sensor types. A capacitive sensor which has the advantage of providing correct results even when bent (in contrast with the resistive sensor, for example) and also detects static forces (in contrast with the piezoelectric sensor) is used as the electrical sensor.

In a more cost-effective solution, however, the gripping pressure can also be effected using pneumoelectrical sensors by means of pressure chambers, in particular in the form of air cushions, which are incorporated in a pocket in each finger of the glove. The pressure is then measured using an electropneumatic converter which is connected to the respective cushion by means of a tube. In order to avoid measuring an overpressure caused just by the finger curvature on its own, it may be expedient to subdivide the cushion of a glove finger into 2 or 3 segments which are connected to one another using a tube.

Each cushion may be at least partially surrounded by a profile of elastic material, the maximum profile height exceeding the height of the cushion in order to protect the cushion from increased pressure and provide the player with more direct contact with the club grip. The profile may be installed in the pocket for the finger cushion and may be in the form of a relatively strong rubber tube, for example.

In order to ensure the dimensional stability of the cushions, it is also possible to partially fill them with an elastic material, in particular foam. The gas-permeable foam is used to keep the air cushions of the pneumoelectrical sensors in a defined form even when the air cushion has not yet been connected to the electropneumatic converter by means of a line. This simplifies the production of the golf training glove according to the invention.

The air cushions comprise, in particular, a plastic film. The tube which is used as a line to connect the air cushion to the electropneumatic converter is preferably welded to the cushion.

In one advantageous refinement of the invention, the sensors provide analog electrical signals which are processed in evaluation electronics following analog/digital conversion. The main task of the evaluation electronics is to use the measured values recorded at the sensors for the individual fingers as a basis for deciding whether the gripping pressure has exceeded a critical threshold value and to signal this, if necessary. In one simple refinement of the invention, a standard threshold value is defined for the sensors of all glove fingers. However, the evaluation electronics preferably allow an individual threshold value comparison for the measured values from each sensor. The different forces on the individual fingers with a correct gripping technique can be taken into account in a precise manner on the basis of the individual threshold value comparison. The threshold value comparison with the analog electrical signals also allows the gripping forces for the left and right hands during the golf swing to be considered in a differentiated manner.

So that brief pressure peaks at individual sensors, which are unavoidable on account of the kinematics of the golf swing or are even desirable, do not trigger incorrect signaling, the evaluation electronics have means for temporally smoothing the measured values. This ensures that only situations in which the threshold value is exceeded for a minimum period of time trigger the signaling. In order to be temporally smoothed, the measured values can be filtered using a low-pass filter, for example. Additionally or alternatively, the evaluation electronics may have means for scaling the measured values. The measured values are either amplified or attenuated as a result of the scaling. This measure makes it possible to take into account the fact that each finger exerts a different pressure on the sensor associated with it in the case of tension which is subjectively felt to be the same. For example, the index finger is stronger than the ring finger, with the result that it may be recommended to amplify the signal for the ring finger in comparison with that for the index finger. On the other hand, the club grip exerts an increased pressure on the little finger at the beginning of the swing. So that this additional pressure on the sensor associated with the little finger is not incorrectly interpreted as an excessively high gripping pressure, it is recommended to slightly attenuate the measured values from this sensor. If the measured value from the sensor on the index finger is taken as a reference point, it has proven advantageous to amplify the measured values from the sensors on the middle and ring fingers and to attenuate the measured value from the sensor on the little finger.

During active play, a golf glove is exposed to a high level of wear, with the result that it must be replaced after some time. However, the evaluation electronics of the golf training glove are subject to virtually no wear. In one advantageous refinement of the invention, the evaluation electronics are therefore releasably connected to the golf training glove. They can be separated from the worn-out golf training glove without being destroyed and can be fitted to a new golf training glove. This new golf training glove contains the electrical sensors or, in the case of pneumoelectrical sensors, the air cushions including the connecting lines to the electropneumatic converter. The electropneumatic converters are preferably likewise releasably connected to the golf training glove and can continue to be used when the latter is replaced.

The releasable evaluation electronics are connected by means of electrical coupling to the leads for the electrical sensors or by coupling the air tubes to the electropneumatic converters.

Incorrect signaling caused by the weight of the club acting on the hand is reduced if the fingers of the glove are subdivided into three segments, the sensors being arranged in the first segment or in the first and second segments, starting from the tip of each glove finger. In this case, it is assumed that the first segment of each glove finger is used to accommodate the distal phalanx, the second segment of each glove finger is used to accommodate the medial phalanx and the third segment of each glove finger is used to accommodate the proximal phalanx.

In order to avoid incorrect signaling on account of incorrect measured values in a manner largely independent of an ideal grip with the smallest possible number of sensors, the sensors are arranged in the first segment of the glove fingers for accommodating the little finger, the ring finger and the middle finger, starting from the tip of each glove finger, and the sensor is arranged in the second segment of the glove finger for accommodating the index finger, starting from the tip of the glove finger. Particularly in the case of pneumoelectrical sensors, it has been found that, with this arrangement of the sensors, the pressure for a wide variety of grips is measured in the most reliable manner and the player does not perceive the sensors to be disruptive. The air cushions of the pneumoelectrical sensors of the little finger, of the ring finger and of the middle finger are as close as possible to the junction with the medial segment, that is to say in the vicinity of the joint for the medial phalanx. For the index finger, it is advantageous to place the air cushion of the electropneumatic sensor in the medial segment, that is to say in the region of the middle medial phalanx, because the index finger encloses the club grip to a lesser extent than the other fingers, with the result that the greatest pressure is exerted by the index finger in the region of the medial phalanx. In addition, the pressure exerted by the opposite thumb is automatically concomitantly measured as a result of this placement since said thumb rests on the opposite side of the club grip opposite the medial phalanx of the index finger in the case of a more or less correct grip. At the same time, this preferred arrangement of the air cushions can ensure that the air cushions of the sensors are loaded over their entire area. If the air cushions are compressed only partially, only some of the air is displaced and an incorrect measured value is consequently recorded.

In another refinement of the invention, the evaluation electronics have means for wirelessly transmitting data, in particular the measured values processed in the evaluation electronics. Data transmission allows the measured values to be logged and processed further using a personal computer and allows errors in the gripping technique to be visualized on the display unit of the latter.

The invention is explained in more detail below using the figures, in which.

Figure 1:
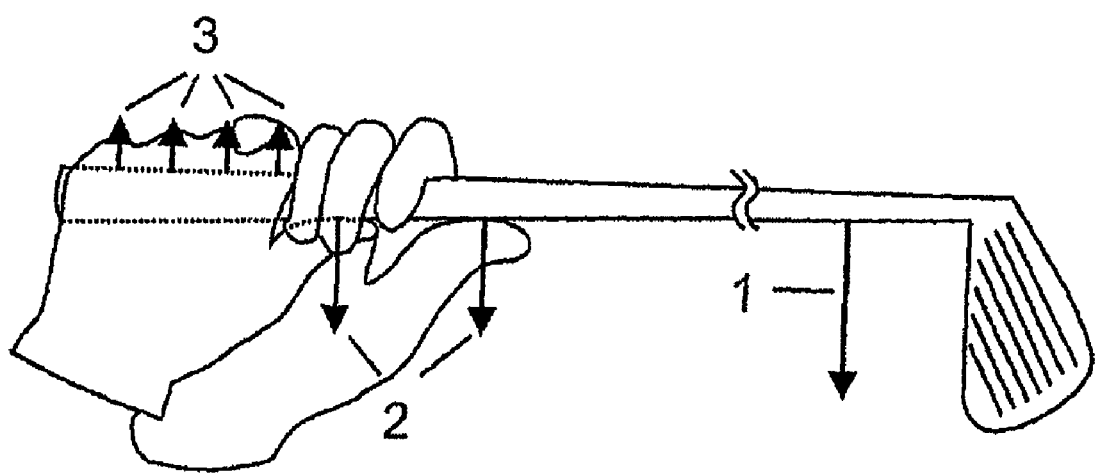
FIG. 1 shows the force distribution at the upper reversal point of a golf swing.

FIG. 1 shows the force distribution at the upper reversal point of the swing, arrow 1 symbolizing the weight force of the club at the center of gravity, the arrows 2 symbolizing the supporting force of the thumbs and the arrows 3 symbolizing the force on the inner surface of the left hand.

FIG. 1 illustrates that, even in the case of a completely relaxed gripping pressure, the weight of the club must be downwardly supported by both thumbs at the upper reversal point of the swing. As a result of the fact that the center of gravity of the club is at a considerable distance from the grip, the force on the thumbs is intensified as a result of a lever effect. Therefore, arranging a sensor in the thumb results in incorrect signaling.

FIG. 1 also illustrates that a great force is exerted on the inner surface of the hand at the upper reversal point of the swing since the inner surface of the left hand upwardly supports the weight of the club. This force is even greater than the force on the thumbs since the only upwardly effective force occurs at this point when the forces are in equilibrium. Therefore, arranging a sensor on the inner surface of the hand likewise results in incorrect signaling at the reversal point of the swing.

Figure 2:
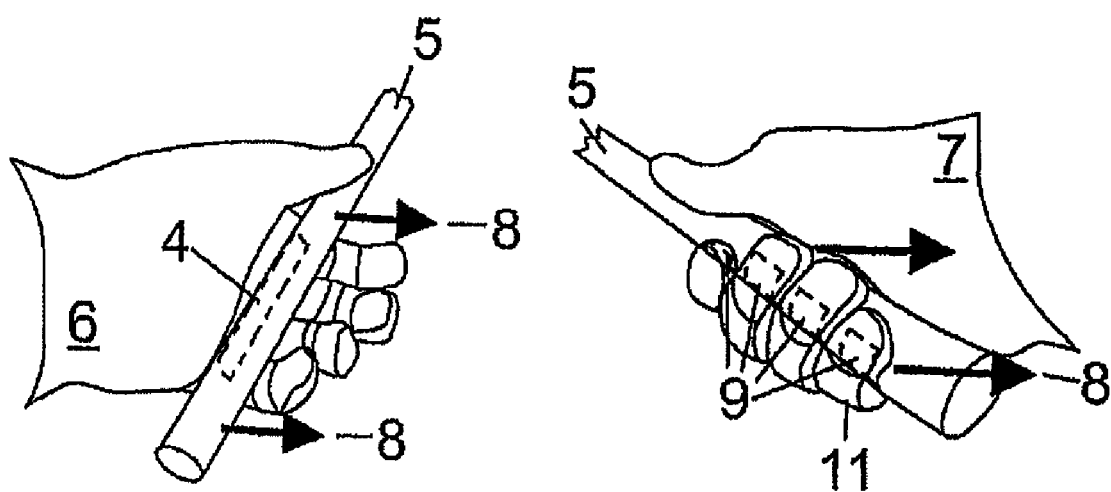
FIG. 2 shows the illustration of correct and incorrect initiation of a swing.

However, the following disadvantages of a sensor 4 on the inner surface of the hand of a golf training glove, which are explained with reference to FIG. 2, are far more serious:

With a correct swinging technique, the club 5 should be pushed away with the left hand 6 at the beginning of the swing and not pulled away with the right hand 7. As a result of incorrectly pulling away with the right hand 7, the fingers automatically tense in order to counteract the inertia of the club 5, while the correct initiation of the swing with the left hand 6 does not build up any harmful stress since all of the fingers can remain relaxed. However, with the correct technique for initiating the swing, a force is exerted on the sensor 4 on the inner surface of the hand as a result of the inertia of the club counter to the direction of movement indicated by the arrows 8 during the upswing, with the result that the sensor 4 is triggered even with a completely relaxed, correct grip. If, in contrast, sensors 9 are installed in the glove fingers 11 of the right hand 7 according to the invention, the incorrect technique for initiating the swing triggers these sensors 9, while the correct swinging technique would not trigger the sensors.

Figure 3:
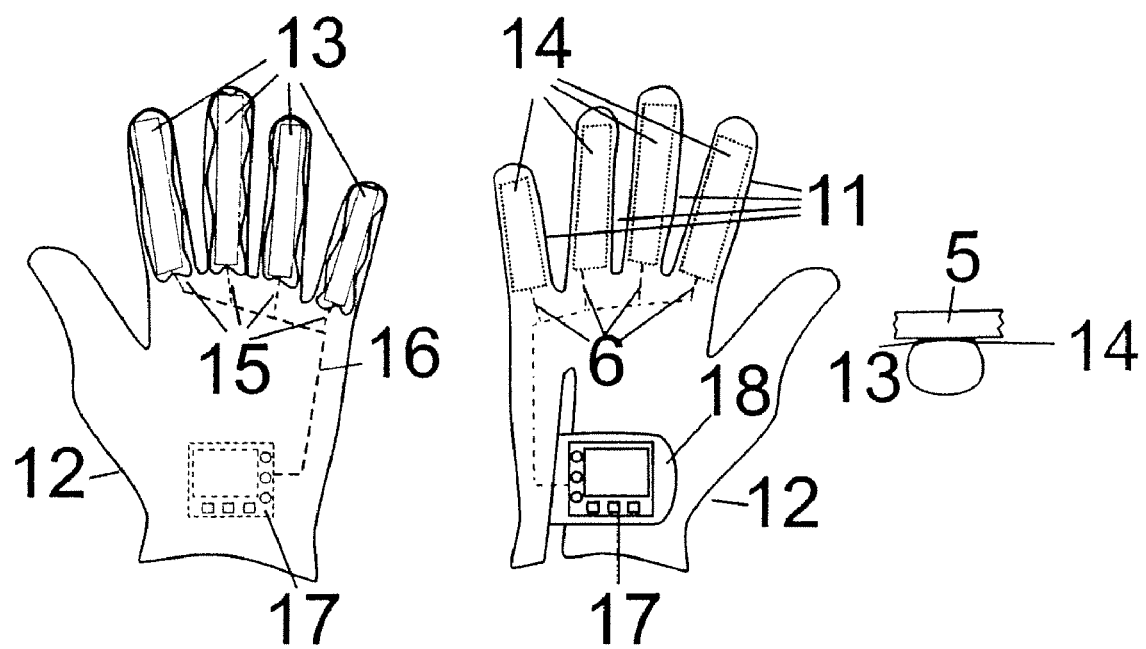
FIG. 3 shows a first exemplary embodiment of a golf training glove according to the invention.
Figure 4:
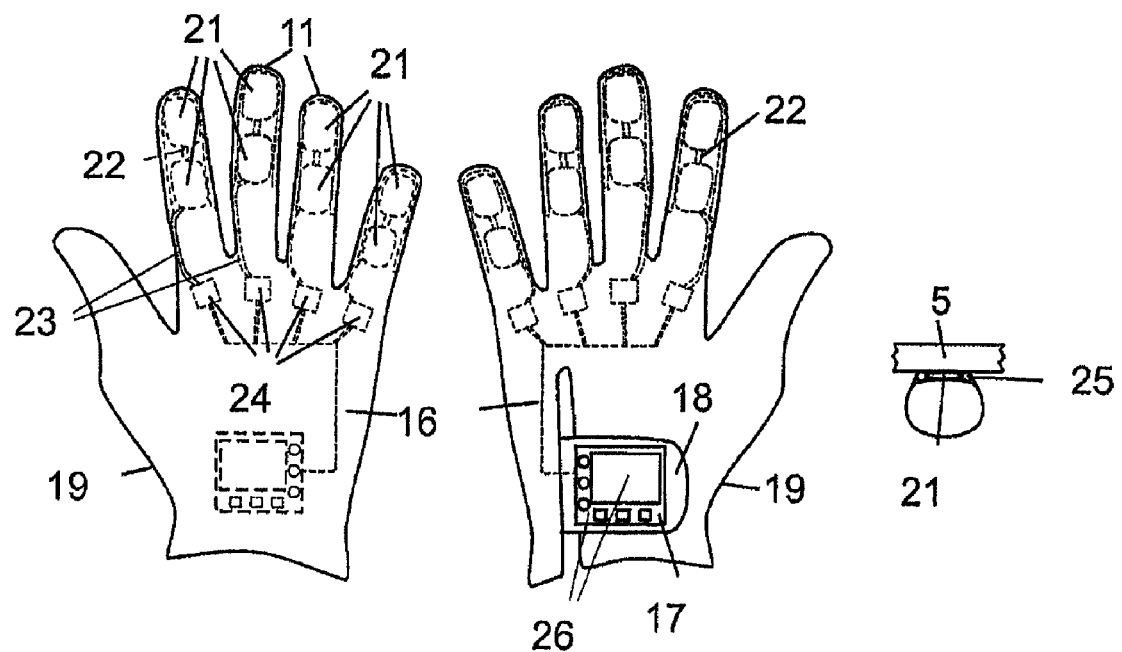
FIG. 4 shows a second exemplary embodiment of a golf training glove according to the invention.

The basic design of a golf training glove according to the invention is illustrated for different sensor technologies in FIGS. 3 and 4 for a left glove 12.

FIG. 3 shows a glove 12 according to the invention having electrical sensors 13 which are arranged on the inside of the glove fingers 11 over the entire length of the latter. The sensors 13 are situated in pockets whose outer skin 14 is indicated on the right of the figure. The connections 15 of the sensors 13 are connected to evaluation electronics 17 by means of connecting lines 16, said evaluation electronics being accommodated in a closure 18 for the glove 12 on the top side of the latter.

FIG. 4 shows a glove 19 in which air cushions 21 of pneumoelectrical sensors 21, 24 are situated only in the first two segments of the glove fingers 11. An elastic bead 25 surrounds the air cushions 21. The club 5 rests on the bead 25 and the air cushions 21. The air cushions 21 are connected to one another, such that they bridge the front two segments of each glove finger, by means of tubes 22. A respective further tube 23 respectively connects each pair of air cushions in a glove finger 11 to an electropneumatic converter 24, each converter 24 in turn being connected to the evaluation electronics 17 in the glove closure 18 by means of electrical connecting lines 16.

As regards the sensors of the glove 12 for the left hand 6, which is illustrated in FIG. 4, all fingers (apart from the thumb) uniformly enclose the grip and can thus be weighted equally.

If, for reasons of cost, only small sensors, that is to say those with only one air cushion for each sensor, are used, they should be in the upper segments of the glove fingers 11. As regards the sensors of the glove for the right hand 7, one sensor in the glove finger 11 for the little finger can be dispensed with for reasons of cost since, in the vast majority of gripping techniques, said finger does not rest on the club.

Irrespective of the technology used, the sensors 21, 24 for each finger provide an analog measured value which is processed further in the evaluation electronics 17 using a digital microcontroller following analog/digital conversion. The task of these evaluation electronics 17 is to use the pressure values determined for the individual fingers as a basis for deciding whether the gripping pressure has exceeded a critical value and to signal this using light, sound or vibration.

The question as to whether an alarm should be triggered depends on the threshold value and on the period of time for which this value is exceeded. It is possible to define a separate threshold value for each individual finger. In any case, at least one joint threshold value for all sensors 21, 24 in the glove fingers 11 can be set in a continuously variable manner or in stages in order to set particular degrees of difficulty (beginner, advanced player). In addition, a distinction may be made between the threshold value for the glove 12 for the left hand 6 and that for the right hand 7.

So that random measurement errors (pressure peaks) and situations in which the threshold value is exceeded only briefly but in a desirable manner (for example when contact is made with the ball or ground) do not trigger incorrect signaling, only situations in which the threshold value is exceeded for a longer period of time should initiate signaling. For this purpose, the sensor values measured can be filtered using a low-pass filter, for example.

Figure 5:
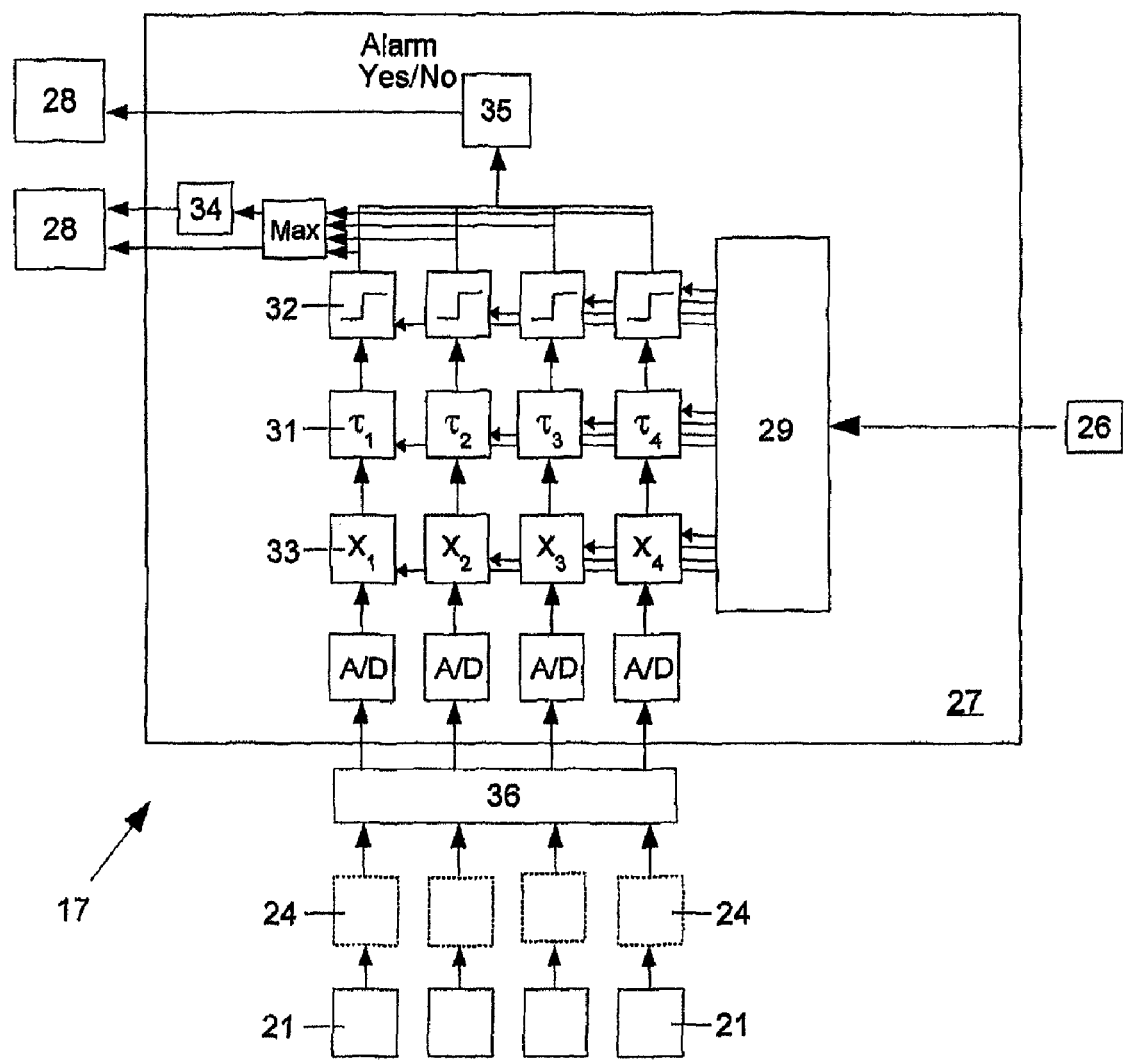
FIG. 5 shows a basic block diagram of evaluation electronics.

FIG. 5 illustrates the basic block diagram of evaluation electronics 17. A microcontroller which is denoted overall using 27 is used to process the measured values and coordinate the input and output elements 26, 28. The inputs are made using buttons which can be seen in FIGS. 3, 4 and 6, while output is effected using optical and acoustic signaling means 28, for example a display or loudspeaker.

A user profile is input to a memory 29, for example a "look-up table", using the buttons of the evaluation electronics 17. The user profile comprises individual threshold values for the measured values recorded by each sensor 21, 24 as well as values for scaling and temporally smoothing the measured values from each sensor 21, 24. The threshold value comparison of the measured values from the sensors 21, 24 is carried out in comparators 32 for the signal path of each individual sensor. Low-pass filters 31 for the temporal smoothing as well as attenuation and amplification elements 33 for the scaling are also situated in the signal path. If one of the comparators 32 determines that the measured value exceeds the threshold value predefined for the respective user profile, this is indicated for each signal path using the signaling means 28. A voltage-controlled oscillator 34 is connected upstream of the acoustic signaling means 28. The voltage-controlled oscillator 34 generates output voltages at different frequencies on the basis of the output signal generated by the comparator 32, said output voltages generating sounds of different levels in a loudspeaker, for example. Therefore, different acoustic signals are generated depending on the extent to which the threshold value is exceeded.

In addition, the outputs of all comparators 32 are connected to an OR circuit 35. The latter likewise uses the further optical/acoustic signaling means 28 to trigger an alarm if only one of the comparators 32 determines that the threshold value has been exceeded.

On the input side, the evaluation electronics 17 have, for each measurement channel, an analog/digital converter A/D which converts the analog measurement signals from the pneumoelectrical converter 24 into digital signals downstream of signal conditioning 36.

The following factors are feasible, for example, as scaling factors X1-X4 for the attenuation and amplification elements 33, where X1 is assigned to the measured values from the sensor of the index finger, X2 is assigned to the measured values from the sensor of the middle finger, X3 is assigned to the measured values from the sensor of the ring finger, and X4 is assigned to the measured values from the sensor of the little finger:

X1=1.0
X2=1.0-1.2
X3=1.0-1.25
X4=0.8-0.95

Attenuation of the little finger is expedient since the club grip exerts an intensified pressure on the little finger during initiation of the swing. So that this additional pressure on the little finger is not incorrectly detected as being an excessively high gripping pressure by the comparator 32, the measured value at the little finger is attenuated, while the measured values at the middle and ring fingers, which are weaker than the index finger, are amplified slightly in comparison with that at the index finger.

Figure 6:
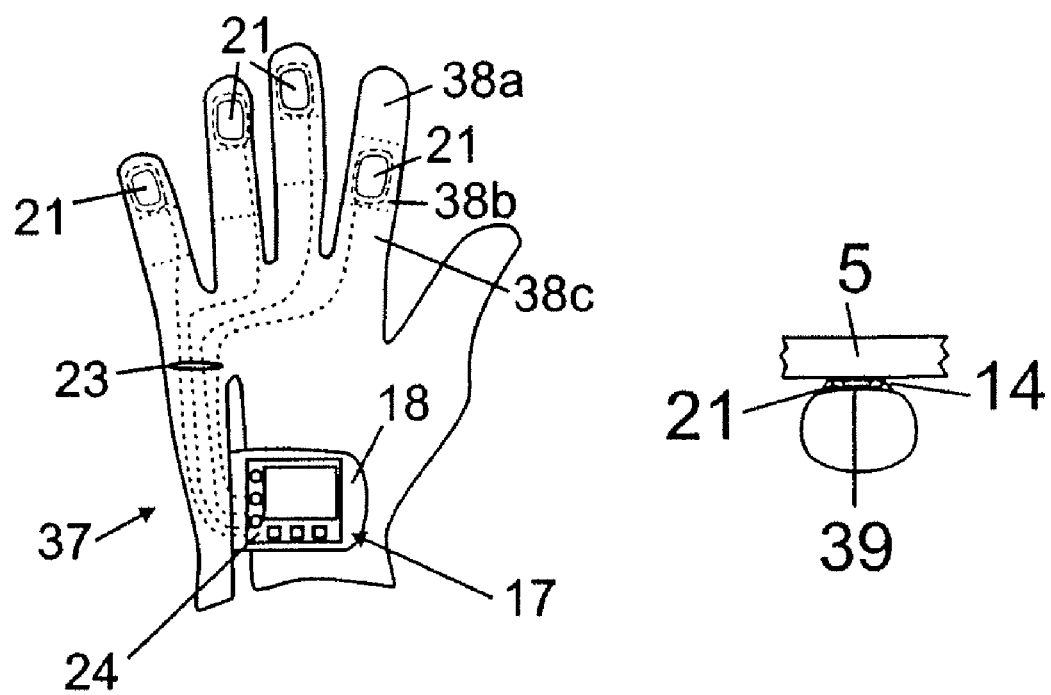
FIG. 6 shows a third exemplary embodiment of a golf training glove according to the invention.

FIG. 6 shows a glove 37 in which the electropneumatic sensors 21, 24 are arranged in such a manner that the pressure exerted on the grip by the player can be detected in a manner largely independent of an ideal grip. The fingers 11 of the glove 37 are subdivided into three segments 38a-c, the air cushions 21 of the sensors 21, 24 being arranged in the first segment 38a of the glove fingers for accommodating the little finger, the ring finger and the middle finger, and the air cushion 21 being arranged in the second segment 38b of the glove finger for accommodating the index finger. The individual air cushions 21 are connected to the converters 24 by means of tubes 23. The pneumoelectrical converters 24 provide analog signals which are processed further in the evaluation electronics 17 according to FIG. 5 following analog/digital conversion.

The air cushions 21 are filled with gas permeable foam 39 which keeps the air cushions 21 in a defined form. In the case of this glove 37 too, the evaluation electronics 17 are integrated in the closure 18 and accordingly have input and output elements 26, 28.

Figure 7:
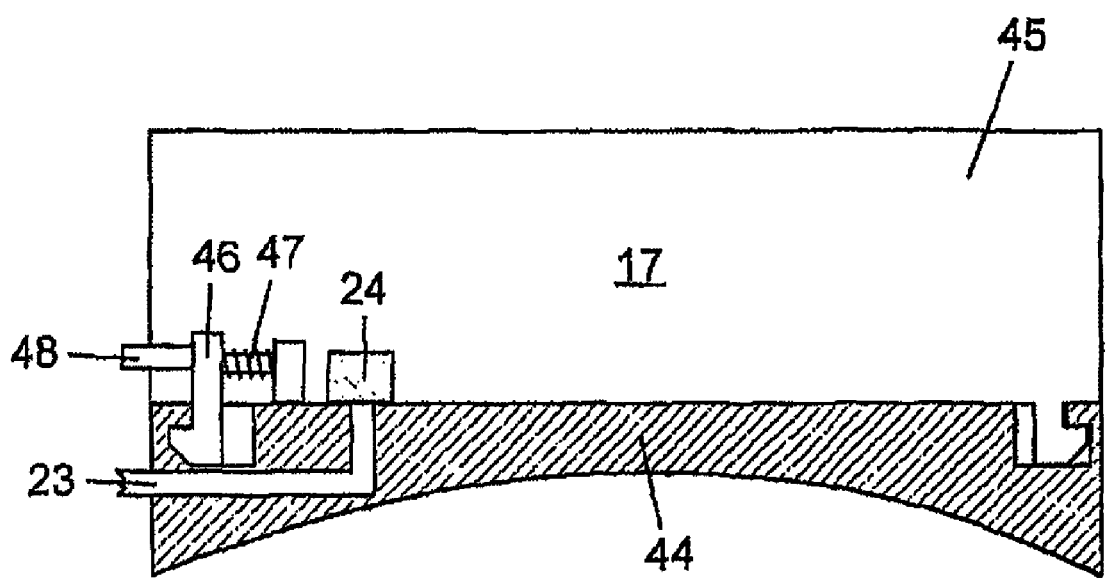
FIG. 7 shows a side view of evaluation electronics which can be releasably connected to the golf training glove.

FIG. 7 finally shows a side view of evaluation electronics 17 which are releasably connected to the glove 12, 19 or 37. For this purpose, a base 44 which is adapted to the contour of the back of the hand is fastened to the top side of the glove 12, 19, 37. The housing 45 which accommodates the evaluation electronics 17 is releasably hooked to the base 44. For this purpose, at least one of the hooks 46 is designed such that it can be moved counter to the force of a spring 47. The movable hook 46 can be displaced by actuating a pin 48 which extends through the wall of the housing 45, with the result that the housing 45 is released.

The pneumoelectrical converters 24 are coupled to the tube lines 23 by virtue of the end sections of the tube lines engaging in corresponding receptacles of the converters 24. In the case of electrical sensors in the glove fingers, the electrical lines leading from the sensors open into contact areas on the surface of the base 44 which interact with corresponding contact areas on the underside of the housing 45.

The removable evaluation electronics 17 can continue to be used when the glove is worn out. Only the relatively inexpensive air cushions 21 including the tubes 23 welded to them are replaced.

LIST OF REFERENCE SYMBOLS

| No. | Designation |
| --- | --- |
| 1. | Weight force of the club |
| 2. | Supporting force of the thumb |
| 3. | Force on the inner surface of the hand |
| 4. | Sensor on the inner surface of the hand |
| 5. | Club |
| 6. | Left hand |
| 7. | Right hand |

-continued

| No. | Designation |
|---|---|
| 8. | Direction of movement in the upswing |
| 9. | Sensor in the glove finger |
| 10. | — |
| 11. | Glove fingers |
| 12. | Glove |
| 13. | Sensor |
| 14. | Outer skin |
| 15. | Connection |
| 16. | Connecting line |
| 17. | Evaluation electronics |
| 18. | Closure |
| 19. | Glove |
| 20. | — |
| 21. | Air cushion |
| 22. | Tube |
| 23. | Tube |
| 24. | Converter |
| 25. | Bead |
| 26. | Input/output element |
| 27. | Microcontroller |
| 28. | Optical/acoustic signaling means |
| 29. | Memory |
| 30. | — |
| 31. | Low-pass filter |
| 32. | Comparators |
| 33. | Attenuation/amplification elements |
| 34. | Voltage-controlled oscillator |
| 35. | OR circuit |
| 36. | Signal conditioning |
| 37. | Glove |
| 38. a)-c) | Segments |
| 39. | Foam |
| 40. | — |
| 41. | Buttons |
| 42. | User profile |
| 43. | Display |
| 44. | Base |
| 45. | Housing |
| 46. | Hook |
| 47. | Spring |
| 48. | Pin |

The invention claimed is:

1. A golf training glove for a golfer for triggering a perceptible signal when the technique used to grip the golf club is incorrect, the golf glove comprising:
a glove having a plurality of fingers for accommodating the golfer's hand, the glove having a thumb, an index finger, a middle finger, a ring finger and a little finger;
a plurality of sensors arranged at least in the glove fingers, the plurality of sensors adapted to measure a grip pressure between the golfer's hand and the club; and
an evaluation electronics device in communication with the plurality of sensors, the electronic device adapted to trigger the perceptive signal when the grip pressure in at least one of the plurality of sensors becomes excessively high in comparison to a threshold value,
wherein the plurality of sensors are located along the index finger, the middle finger and the ring finger of the glove.

2. The golf training glove as claimed in claim 1, wherein a further sensor is arranged in the glove finger for the little finger.

3. The golf training glove as claimed in claim 1 wherein the sensors are located on glove on the inside of the golfer's hand.

4. The golf training glove as claimed in claim 1, wherein the sensors are incorporated in pockets.

5. The golf training glove as claimed in claim 1, wherein the sensors are capacitive sensors.

6. The golf training glove as claimed in claim 1, wherein the sensors are pneumoelectrical sensors.

7. The golf training glove as claimed in claim 6, wherein the each pneumoelectrical sensor includes a plurality of pressure chambers, wherein the plurality of pressure chambers are connected by lines.

8. The golf training glove as claimed in claim 7, wherein each pressure chamber of the pneumoelectrical sensor is connected to an electropneumatic converter by a line, wherein the electropneumatic converter converts the pressure fluctuations in each pressure chamber into analog electrical signals.

9. The golf training glove as claimed in claim 8, wherein each of the electropneumatic converters are releasably connected to the golf training glove.

10. The golf training glove as claimed in claim 7, wherein each pressure chamber of the pneumoelectrical sensor is at least partially filled with an elastic gas-permeable material.

11. The golf training glove as claimed in claim 7, wherein each pressure chamber is at least partially surrounded by a profile of elastic material, the maximum profile height exceeding the height of the pressure chamber.

12. The golf training glove as claimed in claim 1 wherein the evaluation electronics device further scales and smoothes the detected grip pressure.

13. The golf training glove as claimed in claim 1, wherein the evaluation electronic device is releasably connected to the golf training glove.

14. The golf training glove as claimed in claim 1, wherein the fingers of the glove-are subdivided into three segments, in a first segment disposed adjacent a tip of the finger of the glove, a second segments the sensors are disposed in a midportion of the finger of the glove, and a third segment disposed at a base of the glove finger adjacent the golfer's palm, the sensors being arranged in the first or second segments.

15. The golf training glove as claimed in claim 14, wherein a first pressure chamber is arranged in the region of the first segment and a second pressure chamber is arranged in the region of the second segment.

16. The golf training glove as claimed in claim 14, wherein the sensors being arranged in the first segment of the glove fingers of the little finger, the ring finger and the middle finger, and the sensor being arranged in the second segment of the glove finger of the index finger.

17. The golf training glove as claimed in claim 14, wherein the first segment of each glove finger is used to accommodate the distal phalanx of the golfer's hand, the second segment of each glove finger is used to accommodate the medial phalanx of the golfer's hand and the third segment of each glove finger is used to accommodate the proximal phalanx of the golfer's hand.

18. The golf training glove as claimed in claim 1, wherein the evaluation electronics device transmits data wirelessly.

19. A golf training glove for a golfer to signal when the golfer overgrips a golf club, the golf training glove comprising:
a glove having a plurality of fingers for accommodating the golfer's hand, the glove including a plurality of pockets formed along the fingers on the inside of the golfer's hand;
a plurality of pneumoelectical sensors disposed in the plurality of pockets, the pneumoelectrical sensors adapted to measure a grip pressure between the golfer's hand and the golf club; and
an evaluation electronics device located on the back of the golfer's hand and connected with the plurality of pneumoelectrical sensors via a plurality of lines, the evaluation electronics device adapted to signal the golfer when the grip pressure in at least one of the plurality of pneumoelectrical sensors exceeds a threshold value.

20. The golf training glove as claimed in claim 19 wherein the pneumoelectrical sensors are adapted to be removed from the pockets so that the sensors may be placed in a different glove.

21. The golf training glove as claimed in claim 19, wherein the evaluation electronic device is releasably connected to the golf training glove and located on the back of the golfer's hand.

22. A method for signaling a golfer when the golfer overgrips the golf club comprising:
- providing a golf training glove having a plurality of fingers for accommodating the golfer's hand;
- providing a plurality of sensors disposed along the fingers of the golf training glove;
- providing an evaluation electronic device in communication with the plurality of sensors;
- sensing the grip pressure between the golfer's hand and the golf club with the plurality of sensors;
- comparing the grip pressure to a threshold value with the evaluation electronic device; and
- signaling the golfer when the grip pressure of at least one of the plurality of sensors exceeds the threshold value.

* * * * *